United States Patent [19]

Oslapas et al.

[11] 3,981,982

[45] Sept. 21, 1976

[54] RADIOIMMUNOASSAY FOR DETERMINING THE DIGOXIN CONTENT OF A SAMPLE

[75] Inventors: Raymond Oslapas, Libertyville; Thomas Raymond Herrin, Waukegan, both of Ill.

[73] Assignee: Abbott Laboratories, North Chicago, Ill.

[22] Filed: Sept. 11, 1974

[21] Appl. No.: 505,185

[52] U.S. Cl. .............................. 424/1.5; 23/230 B; 260/239.57; 424/8; 424/12

[51] Int. Cl.² .................... G01N 33/00; G21H 5/02; C07J 19/00

[58] Field of Search ............... 23/230 B; 424/1, 1.5, 424/8, 12; 260/239.57

[56] References Cited

FOREIGN PATENTS OR APPLICATIONS 459,997 9/1968 Switzerland .................. 260/239.57

OTHER PUBLICATIONS

Evered et al., Nuclear Science Abstracts, vol. 25, No. 2, Jan. 31, 1971, p. 245, Item No. 2522.

Johnston et al., Nuclear Science Abstracts, vol. 26, No. 15, Aug. 15, 1972, p. 3538, Item No. 36471.

Falch, Nuclear Science Abstracts, vol. 29, No. 8, Apr. 30, 1974, p. 1805, Item No. 18679.

*Primary Examiner*—Benjamin R. Padgett
*Assistant Examiner*—Christine M. Nucker
*Attorney, Agent, or Firm*—Gildo E. Fato; Robert L. Niblack

[57] ABSTRACT

A competitive radioimmunoassay for the measurement of digoxin in a serum sample in which the non-radioactive digoxin competes with a constant amount of a radioactively labeled digoxin tyramine analog comprising 3-O-(4-Hydroxyphenethylcarbamoyl) digoxigenin for binding cites on a limited amount of digoxin antibody. The percentage of the radioactively labeled digoxin which is bound to the antibody is inversely proportional to the concentration of digoxin in the serum sample. The concentration of digoxin in the serum is determined by the comparison with standards containing measured amounts of unlabeled digoxin.

7 Claims, 1 Drawing Figure

CHEMICAL AND BIOLOGICAL PRINCIPLES OF THE PROCEDURE (RADIOIMMUNOASSAY)
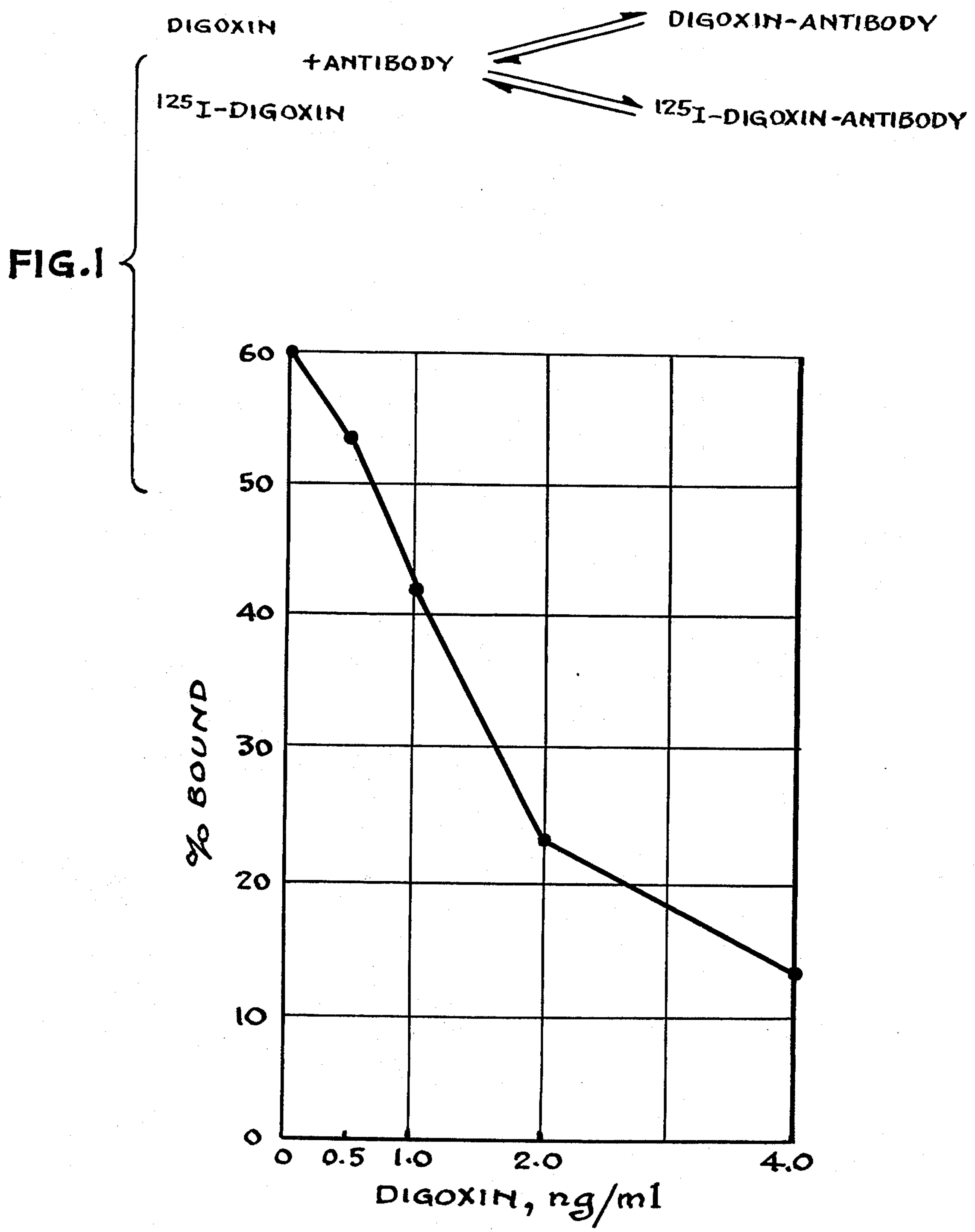

RADIOIMMUNOASSAY FOR DETERMINING THE DIGOXIN CONTENT OF A SAMPLE

BACKGROUND OF THE INVENTION

As compared with conventional analytical methods, the radioimmunoassay offers several advantages, particularly extreme sensitivity and high specificity. With conventional analytical methods, it is difficult to measure the minute amounts of digoxin in serum, usually less than five nanograms per milliliter (ng/ml). Radioimmunoassay procedures are based upon the characteristics that an antibody binds equally to labeled or unlabeled antigen, for example. The concentration of the nonlabeled form in the solution determines the relative amount of labeled or nonlabeled antigen which will bind to antibody. By keeping the concentration of antibody and labeled antigen constant and conducting the radioimmunoassay procedure using a series of known amounts of nonlabeled antigen, a standard curve can be constructed. Subsequently, when an unknown amount of antigen in a serum sample is reacted in the same way, its concentration can be determined by relating the value obtained to the standard curve. Accordingly, levels of antigen in serum may be measured in nanograms.

There are four requisites for a radioimmunoassay procedure: (1) a highly purified antigen; (2) a specific antibody (antiserum) produced by an injection of that antigen into another animal species; (3) radioactively labeled purified antigen or antigen derivative having a previously determined specific activity; and (4) a satisfactory method for the separation of the antigen-antibody complex from the free antigen. Free antigen can be separated from the antigen bound to the antibody and, depending on the method of separation, either free or bound antigen can be measured by determining the radioactivity.

Yalow, R.S. and Berson, S.A. in the *Journal of Clinical Investigation*, Vol. 39, Page 1157, 1960, described the first complete radioimmunoassay procedure. T. W. Smith et al. in the *New England Journal of Medicine*, Vol. 281, Page 1212, 1969, describes a radioimmunoassay for digoxin in which $^3$H-digoxin was used as the radioactive tracer, this tracer requiring a liquid scintillation counting fluid.

SUMMARY OF THE INVENTION

Described is a competitive radioimmunoassay in which non-radioactive digoxin in a serum sample competes with a constant amount of $I^{125}$ digoxin tyramine analog for binding cites on a limited amount of digoxin antibody. The percentage or portion of the radioactivity labeled digoxin which is bound to the antibody is inversely proportional to the concentration of digoxin in the serum sample. The antibody bound digoxin, both radioactive and non-radioactive is separated from unbound digoxin and the radioactivity of the complex is measured with a well-type gamma scintillation counter. The concentration of digoxin in the serum is determined by comparison with standards containing measured amounts of unlabeled digoxin. The use of $I^{125}$ digoxin tyramine analog simplifies the procedure, obviating the need for liquid scintillation counting fluid which must be used with $^3$H-digoxin.

In the radioimmunoassay of the present invention, the use of polyethylene glycol is preferred to separate the bound, labeled digoxin tyramine analog from the free digoxin although ethanol or ammonium sulfate can be used. After incubation of the antigen and antibody, a predetermined amount of polyethylene glycol is added and the mixture is agitated. Subsequently, the antibody-bound digoxin is precipitated and separated by centrifugation. The radioactivity remaining in the precipitate is measured to determine the amount of $I^{125}$ digoxin tyramine analog which is bound to the antibody. This amount will be inversely proportional with the quantity of nonlabeled antigen present in the serum sample.

DRAWINGS

The invention will be described in conjunction with the following drawings in which:

FIG. 1 represents a standard curve prepared in accordance with the method of the present invention together with a representation of the principles of the radioimmunoassay.

DETAILED DESCRIPTION

The radioimmunoassay of the present invention measures digoxin in the serum sample. The digoxin in a serum sample competes with a constant amount of a radioactively labeled digoxin tyramine analog for binding cites on a limited amount of digoxin antibody. The digoxin tyramine analog comprises 3-0-(4-Hydroxyphenethylcarbamoyl) digoxigenin prepared as hereinafter described. The digoxin tyramine analog is labeled with a radioactive isotope, employing conventional procedures. Iodine-$I^{125}$ is preferred as the labeling agent because of its advantageous half life but other radionuclides such as iodine$^{131}$, phosphorus$^{32}$ and tritium can also be used to radioactively label the reagent. The use of this tracer simplifies the procedure, obviating the need for liquid scintillation counting fluid which must be used with prior tracers such as $^3$H-digoxin.

Preparation of the digoxin tyramine analog is accomplished in the following manner.

EXAMPLE I

Preparation of 3-0-(4-Hydroxyphenethylcarbamoyl) Digoxigenin

12-Acetyldigoxigenin.

The procedure described by A. Yamada in Ch. Pharm. Bull., Tokyo, Vol. 8, Page 18, 1960, was used to prepare the 12-acetyl derivative. To a solution of 2.00 g. digoxin in 28 ml. of pyridine was added 26 ml. of acetic anhydride and the solution heated at 100° (oil bath temperature) for 4 hours. The solvent was removed at a reduced pressure and most of the last traces of solvent were removed from the residue by azeotroping with toluene. The crude penta-acetate was used in the hydrolysis step without further purification. The penta-acetyldigoxin was dissolved in 200 ml. of methanol and 200 ml. of 0.10 N hydrochloric acid added and the mixture refluxed for 45 minutes, cooled to room temperature and concentrated at reduced pressure until a precipitate formed. The mixture was extracted with chloroform and the chloroform layer dried with magnesium sulfate, concentrated at reduced pressure and the residue crystallized from acetone-ether to give 472 mg., mp. 273°–278° of first crop. A second crop of 240 mg., mp. 270°–283° was obtained from the mother liquor using acetone-ether-hexane as the solvent. Both crops were of acceptable purity for the next step.

3-Chloroformyldigoxigenin.

12-Acetyldigoxigenin 712 mg., 1.648 mmoles, was added to 50 ml. of methylene chloride and 50 $\mu$l of dry dimethylacetamide added and the reaction flask chilled in an ice bath while phosgene and nitrogen were alternately passed through the mixture for seven hours. The solvent was removed at reduced pressure and the residue triturated with ether. The ether was removed and the residue dissolved in acetone and treated with charcoal and filter-aid. Ether was added to the clear solution until the solution became slightly murky at which point the mixture was filtered and allowed to cool to room temperature. The yield of first crop was 318 mg., mp. 144° (decomp.), second crop 81 mg., mp. 143° (decomp.) and third crop 25 mg., mp. 142° (decomp.). The first crop gave an acceptable CHN analysis and all three crops (424 mg., 51.9% yield) were suitable for the next step.

12-Acetyl-3-0-(4-hydroxyphenethylcarbamoyl) digoxigenin.

3-Chloroformyl-digoxigenin, 355 mg., 0.717 mmoles, was added to a mixture of 200 mg. (1.44 mmoles) of tyramine in 50 ml. of freshly distilled tetrahydrofuran cooled to 5°. The reaction mixture was allowed to warm gradually to room temperature and stirred overnight. The solvent was removed and the residue dissolved in a mixture of chloroform-water. The chloroform layer was separated, washed with water, dried over magnesium sulfate and evaporated. The residue was chromatographed on 40 g. of magnesium silicate and the desired product eluted with 10% methanol-benzene to give 325 mg. of product. This material gave a correct elemental analysis.

3-0-(4-Hydroxyphenethylcarbamoyl) digoxigenin

To a solution of 200 mg. of 12-acetyl-3-0-(4-hydroxyphenethylcarbamoyl) digoxigenin in 20 ml. of 50% aqueous methanol was added 2.0 ml. of triethylamine and the solution stirred 25 hours at room temperature. The solution was concentrated at reduced pressure until a precipitate formed. The mixture was thoroughly extracted with ethyl acetate and the ethyl acetate layer washed with water, dried over magnesium sulfate and the solvent removed at reduced pressure. The residue, 147 mg., was purified by preparative thin layer chromatography. The purified material was dissolved in a minimum amount of methanol and allowed to stand. An amorphorous solid precipitated, 54 mg., which by tlc was greater than 90% pure.

The following description illustrates a method for conducting the radioimmunoassay, the reagents used being as follows:

1. $I^{125}$-digoxin tyramine analog solution in an alcohol-phosphate saline buffer and having a radioactivity level of approximately 1 microcurie per vial.

2. Digoxin standards for preparation of a standard curve and comprising five vials containing 0.0, 0.5, 1.0, 2.0 and 4.0 nanograms per milliliter digoxin in normal human serum. 0.2% sodium azide is used as a preservative.

3. Digoxin antiserum obtained from rabbits in phosphate-saline buffer containing 0.1% buffer serum albumin. 0.2% sodium azide is used as a preservative.

4. Polyethylene glycol, 18% solution in 0.09M barbital buffer.

From these reagents a test kit can be prepared, a kit for conducting 100 tests containing:

One vial (10 ml.) $I^{125}$ digoxin tyramine analog solution having an activity of approximately 1 microcurie per vial. 0.2% sodium azide is added as a preservative;

Five vials (1.5 ml. each) digoxin standards, containing 0.0, 0.5, 1.0, 2.0 and 4.0 nanograms per milliliter digoxin in normal human serum;

Three vials (10 ml. each) digoxin antiserum and containing 0.2% sodium azide as a preservative;

One bottle (200 ml.) polyethylene glycol, 18% solution in 0.09M barbital buffer; and One-hundred test tubes.

The test procedure is conducted as follows. At least six hours after administration of a dose of digoxin, a sample of blood is withdrawn from the patient. The blood is allowed to clot and the serum is separated therefrom. If the radioimmunoassay procedure is to be conducted more than 24 hours after the serum has been separated, it should be stored in a frozen condition. At the time the radioimmunoassay is to be conducted, the serum should be brought to room temperature.

A standard curve should be prepared at the same time that a group of samples is assayed. All test kit reagents, including the polyethylene glycol reagents and the serum samples are brought to room temperature. The entire kit should be stored at 2° to 8°C. when not in use. Tubes for performance of the assay are labeled as follows:

a. Tubes 1 and 2, containing aliquots of $I^{125}$ digoxin tyramine analog solution are used in determining total radioactivity of the tracer reagent.

b. Tubes 3 through 12 containing known amounts of digoxin are used to prepare the standard curve. Tubes 3 and 4, 0.0 nanograms per milliliter digoxin. Tubes 5 and 6, 0.5 nanograms per milliliter digoxin. Tubes 7 and 8, 1.0 nanograms per milliliter digoxin. Tubes 9 and 10, 2.0 nanograms per milliliter digoxin. Tubes 11 and 12, 4.0 nanograms per milliliter digoxin.

c. Tubes 13 etc., containing the serum samples being assayed, in duplicate.

0.1 ml. of known amounts digoxin are pipetted into tubes 3 to 12 and 0.1 ml. of samples to be assayed, in duplicate, are pipetted into the tubes beginning with number 13. 0.3 ml. of digoxin antiserum is placed into each of the tubes, both standards and unknown samples. The tubes are shaken to mix the reagents therein. One-tenth of a milliliter of the $I^{125}$ digoxin tyramine analog is placed into each of the tubes and the tubes again shaken to mix the reagents. All of the tubes thereafter incubated at room temperature, (20° to 30°C.) for a period of about thirty minutes. After incubation, the tubes (1 and 2) containing the labeled reagent are set aside and 2 ml. of an 18% polyethylene glycol solution is added to each of the remaining tubes. The contents of the tubes are mixed vigorously for about 10 seconds and then centrifuged for 10 minutes at 2700 to 3300 RPM at room temperature. The supernatant solution is decanted and the radioactivity remaining in the precipitate is measured in a conventional well scintillation counter.

Employing the above described procedure, values are obtained in the following manner. The mean value of radioactivity for the duplicate tubes 1 and 2 representing the total radioactivity of the tracer reagent is calculated. The percentage or portion of the radioactively labeled digoxin tyramine analog which is bound to the antibody for each standard or unknown sample is calculated as follows:

$$\% \text{ digoxin bound} = \frac{\text{radioactivity of the precipitate in } CPM}{\text{radioactivity of the tracer reagent}} \times 100$$

A standard curve, as illustrated in Figure 1, is plotted on linear graph paper using percent bound values on the $y$ axis and the various concentrations of digoxin standards on the $x$ axis. The points are connected with straight lines to construct the curve.

For an unknown sample, the percentage or portion of the radioactively labeled digoxin which is bound to the antibody (percent bound) is located on the $y$-axis of the standard curve and a horizontal line is extended to the curve from this point. At the point of intersection of the curve, a vertical line is extended to the $x$-axis, the intersection of the vertical line with the $x$-axis representing the concentration of serum digoxin in the unknown sample.

Table I represents a typical assay employing the procedure of the present invention, tubes 1 and 2 representing the total radioactivity of the tracer reagent; tubes 3 through 12 containing known amounts of digoxin, the values thereof being used to prepare the standard curve of Fig. 1 and tubes 13 through 22 containing the unknown samples being measured.

TABLE I

| Tube No. | Concentration or Unknown No. | | cpm | Percent Bound | Average % Bound | ng/ml from Std. Curve | Average ng/ml |
|---|---|---|---|---|---|---|---|
| 1 | | | 10457 | | | | |
| | Total Count | | | | | | |
| 2 | | Average = | 10151 / 10304 | | | | |
| 3 | 0.0 | | 6100 | 59.2 | | | |
| | | | | | 59.7 | | |
| 4 | 0.0 | | 6203 | 60.2 | | | |
| 5 | 0.5 | | 5541 | 53.8 | | | |
| | | | | | 52.9 | | |
| 6 | 0.5 | | 5365 | 52.1 | | | |
| 7 | 1.0 | | 4273 | 41.5 | | | |
| | | | | | 41.5 | | |
| 8 | 1.0 | | 4277 | 41.5 | | | |
| 9 | 2.0 | | 2316 | 22.5 | | | |
| | | | | | 22.9 | | |
| 10 | 2.0 | | 2410 | 23.4 | | | |
| 11 | 4.0 | | 1316 | 12.8 | | | |
| | | | | | 12.9 | | |
| 12 | 4.0 | | 1334 | 12.9 | | | |
| 13 | No. 14 | | 1804 | 17.5 | | 3.08 | |
| | | | | | 17.7 | | 3.04 |
| 14 | No. 14 | | 1849 | 17.9 | | 3.00 | |
| 15 | No. 15 | | 6525 | 63.3 | | | |
| | | | | | 64.1 | not detectable | |
| 16 | No. 15 | | 6695 | 65.0 | | | |
| 17 | No. 16 | | 2589 | 25.1 | | 1.88 | |
| | | | | | 25.3 | | 1.87 |
| 18 | No. 16 | | 2625 | 25.5 | | 1.86 | |
| 19 | No. 17 | | 5230 | 50.8 | | 0.60 | |
| | | | | | 49.6 | | 0.64 |
| 20 | No. 17 | | 5002 | 48.5 | | 0.68 | |
| 21 | No. 18 | | 2523 | 24.5 | | 1.92 | |
| | | | | | 24.4 | | 1.93 |
| 22 | No. 18 | | 2502 | 24.3 | | 1.94 | |

Table II illustrates the accuracy, precision and reproducibilty of the method of the present invention.

TABLE II

Specific Performance Characteristics

The following parameters were evaluated with the method and kit of the present invention and results are summarized as follows:

Accuracy:

Three serum samples representing low to high range of digoxin, in ng/ml, were evaluated versus standard curves prepared by the method of the present invention and U.S.P. Reference Standard.

| | Samples (ng/ml) | | | |
|---|---|---|---|---|
| Standard Source | 1 | 2 | 3 | Overall |
| U.S.P. | 0.70 | 1.95 | 3.80 | |
| $I^{125}$ Digoxin Tyramine Analog | 0.70 | 1.95 | 3.70 | |
| Accuracy | 100% | 100% | 97.3% | 99.1% |

Precision:

Three serum samples representing low to high range of digoxin, in ng/ml, assayed on 43 separate occasions, in five different laboratories.

| | Laboratory | | | | | Combined |
|---|---|---|---|---|---|---|
| | 1 | 2 | 3 | 4 | 5 | Results |
| Low Sample: | | | | | | |
| Mean (ng/ml) | 0.62 | 0.63 | 0.64 | 0.60 | 0.57 | 0.61 |
| S.D. | 0.12 | 0.05 | 0.09 | 0.08 | 0.11 | 0.10 |
| Medium Sample: | | | | | | |
| Mean (ng/ml) | 2.00 | 1.90 | 2.00 | 1.90 | 2.00 | 1.97 |
| S.D. | 0.22 | 0.08 | 0.06 | 0.17 | 0.19 | 0.17 |
| High Sample: | | | | | | |

TABLE II-continued

| | | | | | | |
|---|---|---|---|---|---|---|
| Mean (ng/ml) | 3.70 | 3.70 | 3.70 | 3.40 | 3.90 | 3.71 |
| S.D. | 0.30 | 0.17 | 0.17 | 0.38 | 0.16 | 0.29 |
| Number of Determinations: | 19 | 6 | 5 | 6 | 7 | 43 |

Reproducibility:
Replicates of 2 Panel Samples were assayed by two technicians in the same laboratory. Fifteen replicate samples were used.

| | Technician I | | Technician II | |
|---|---|---|---|---|
| Sample | % Bound S.D. | %C.V. | % Bound S.D. | %C.V. |
| 1 | 44.1 ± 1.0 | 2.35 | 43.6 ± 1.26 | 2.89 |
| 2 | 21.5 ± 0.5 | 2.28* | 20.1 ± 0.51 | 2.54 |

*only 14 replicates
S.D. = Standard Deviation
C.V. = Coefficient of Deviation

With respect to sensitivity, the method of the present invention will measure digoxin concentrations from approximately 0.25 ng/ml to an upper level of approximately 4 ng/ml.

The digoxin concentration as determined by the method of the present invention is used as an adjunct in diagnosis in conjunction with other data and symptoms available to the physician. The value of 2 ng/ml of digoxin has been suggested as the approximate toxic threshold (H. M. Part et al., Clin. Evaluation of Radioimmunoassay of Digoxin, J. of NUCL. Med., Vol. 14, Page 531, 1973) but digoxin levels are highly dependent upon patient variability, renal function, patient tolerance and/or sensitivity to the drug, time after digoxin administration, dose level and the like. Consequently test values obtained should be correlated with established patient diagnosis.

What we claim is:

1. A method of measuring the digoxin content of a serum sample which comprises the steps of:

a. adding digoxin antibody and a tracer amount of radioactively labeled 3-0-(4-Hydroxyphenethylcarbamoyl) digoxigenin reagent to said serum sample to form a mixture;

b. incubating said mixture to permit the digoxin in the sample and said radioactively labeled reagent to bind to the digoxin antibody;

c. adding a precipitating agent to the mixture to facilitate the formation of a precipitate and thereby separate the bound labeled digoxin from the free digoxin;

d. separating the supernatant liquid from the precipitate which is formed; and e. measuring the radioactivity remaining in the precipitate.

2. The method of claim 1 including the steps of preparing a standard curve from samples containing known amounts of digoxin and comparing the radioactivity obtained in step (e) with said standard curve to determine the amount of digoxin in said sample.

3. The method of claim 2 wherein said precipitating agent is selected from the group consisting of polyethylene glycol, ethanol and ammonium sulfate.

4. The method of claim 3 wherein the precipitating agent is polyethylene glycol.

5. The method of claim 4 wherein said mixture is incubated at room temperature for about thirty minutes.

6. A compound selected from the group consisting of 3-Chloroformyldigoxigenin and 3-0-(4-Hydroxyphenethylcarbamoyl) digoxigenin.

7. The compound 3-0-(4-Hydroxyphenethylcarbamoyl) digoxigenin.

* * * * *